(12) United States Patent
Peters et al.

(10) Patent No.: US 7,132,836 B2
(45) Date of Patent: Nov. 7, 2006

(54) MICROWAVE MEASURING ARRANGEMENT FOR PRODUCT DENSITY MEASUREMENT

(75) Inventors: Steffen Peters, Linnich (DE); Reinhard Knöchel, Elmshorn (DE); Wolfgang Taute, Laboe (DE); Claas Döscher, Hamburg (DE)

(73) Assignee: Trützschler GmbH & Co. KG, Mönchengladbach (DE)

( * ) Notice: Subject to any disclaimer, the term of this patent is extended or adjusted under 35 U.S.C. 154(b) by 0 days.

(21) Appl. No.: 10/810,890

(22) Filed: Mar. 29, 2004

(65) Prior Publication Data
US 2004/0189324 A1    Sep. 30, 2004

(30) Foreign Application Priority Data
Mar. 27, 2003    (DE) ................. 103 13 964

(51) Int. Cl.
*G01R 27/04* (2006.01)
*G01R 27/32* (2006.01)
(52) U.S. Cl. ........................ 324/637; 324/636
(58) Field of Classification Search ......... 324/632–642
See application file for complete search history.

(56) References Cited

U.S. PATENT DOCUMENTS

| 4,104,585 A | 8/1978 | Schofield |
| 5,421,190 A | 6/1995 | Brändle et al. |
| 5,736,864 A | 4/1998 | Möller |
| 5,977,780 A * | 11/1999 | Herrmann ............... 324/640 |
| 6,476,619 B1 * | 11/2002 | Moshe et al. ............ 324/634 |
| 6,747,460 B1 | 6/2004 | Moller et al. ............ 324/636 |
| 6,837,122 B1 * | 1/2005 | Herrmann et al. ........ 73/865 |
| 2003/0150266 A1 | 8/2003 | Dammig et al. |

FOREIGN PATENT DOCUMENTS

| EP | 0 582 045 B1 | 2/1994 |
| EP | 0 753 755 A2 | 1/1997 |
| EP | 0 940 672 A | 9/1999 |
| EP | 0 967 479 A2 | 12/1999 |
| EP | 1 331 476 A1 | 7/2003 |
| WO | WO 00/12974 A1 | 3/2000 |
| WO | WO 00/55606 A2 | 9/2000 |

* cited by examiner

*Primary Examiner*—Anjan Deb
*Assistant Examiner*—Jeff Natalini
(74) *Attorney, Agent, or Firm*—Venable LLP; Robert Kinberg; Ryan M. Flandro

(57) ABSTRACT

The invention relates to a measuring arrangement for measuring the density of a product by means of microwaves. The measuring arrangement comprises a first microwave resonator, from which, in operation, microwaves enter a product area, and a device for compensating for environmental influences and disturbance variables affecting the measuring signal of the first microwave resonator. According to the invention, the compensation device comprises a second microwave resonator, which is shielded towards the product area with respect to microwave radiation.

17 Claims, 6 Drawing Sheets

MICROWAVE MEASURING ARRANGEMENT FOR PRODUCT DENSITY MEASUREMENT

CROSS REFERENCE TO RELATED APPLICATION

This application claims the priority of German Patent Application No. 103 13 964.8, which is incorporated herein by reference.

BACKGROUND OF THE INVENTION

The invention relates to a measuring arrangement for measuring the density of a product by means of microwaves.

Certain known devices comprise a first microwave resonator, from which, in operation, microwaves enter a product area. When measuring density using such a measuring arrangement, the measuring variables used, in particular the resonant frequency and the width of the resonance curve, are dependent on different environmental influences and disturbance variables in the first resonator. In order to compensate for the influences, such as the temperature of the resonator, on the systematic measuring error, it is known to provide a temperature sensor at a specific point of the first resonator and to carry out a computational correction by means of the measured temperature. Since the temperature in the first resonator is determined only at one point, the accuracy of the compensation in the first resonator is limited, especially in the case of a spatially non-homogeneous and/or time-variant temperature distribution.

Generally speaking, to compensate, for example, for the effects of temperature, it is known to use different materials, in the present case for the first resonator, having temperature coefficients of opposite signs. Apart from increased manufacturing costs, however, the transition points between the different materials in particular can have an adverse effect in microwave technology. The use of special alloys and composite materials having thermal expansion coefficients close to or equal to zero is also known. These too involve increased manufacturing costs.

It is an aim of the invention to provide an apparatus and method of the kind mentioned above in which the measuring error caused by different environmental influences and by internal and external disturbance variables in the first resonator can be reduced.

SUMMARY OF THE INVENTION

The present invention provides a measuring device for monitoring a material and determining a parameter that is related to the dielectric properties of the material, comprising a product area for receiving the product, a first microwave resonator from which, in operation, microwaves can enter the product area, and a compensation device for compensating for environmental influences, the compensation device comprising a second microwave resonator which is shielded from the product area in respect of microwave radiation.

Some of the terms used will first be explained.

"Resonator" relates to a spatial region in which a standing microwave field is able to form. The resonator can be a closed or a substantially closed cavity resonator or an open resonator.

A product of which the density is being measured is arranged in an area called a "product area", which, when the measuring device is operative, is in a fixed spatial relationship with the area of the first resonator. The product area can extend partially or completely within the first resonator area; alternatively, it can be spatially separate from the first resonator area. In the latter case, the product area can be located adjacent to the first resonator area; alternatively, it can be arranged spatially remote therefrom, and the field can be directed via a line from the resonator to the product area. The microwaves enter the product area in order to interact with the product. Normally, the first microwave resonator is therefore permeable to microwaves towards the product area. The product can be a consecutive and/or continuous stream of product, for example, fibre material, such as a fibre sliver, a fibre web, fibre flocks or individual fibres in spinning preparation machines, or a strand of tobacco in a cigarette-making machine.

In accordance with the invention, the measured variables determined with the second resonator are not —by virtue of the fact that it has microwave shielding towards the product area—affected by the interaction of the microwave field with the product, and are not directly affected by the dielectric constant of the product. Because the measured variables of the first resonator are suitably related to the corresponding measured variables of the second resonator, the effect of environmental influences and disturbance variables, which affect the measuring signal of both resonators, can therefore be compensated. One of these environmental influences and disturbance variables is, for example, the thermal effect of the environment, such as the heat load emanating from the product. The invention has recognised, for example, that the temperature distribution in the first resonator can be spatially non-homogeneous and/or time-variant. As a consequence of this knowledge, the invention permits the measurement, for example, of an integrated temperature, that is, a temperature averaged over a region that corresponds in respect of its arrangement relative to the product area to the first resonator area and therefore has substantially the same temperature distribution as this. This contrasts with a temperature measurement in a region of small extent in relation to the extent of the first resonator.

Especially in the case of time-variant, non-homogenously occurring environmental influences and disturbance variables, the conventional measurement of the temperature of the first resonator at one point, for example, may lead in the individual case to a distorted measuring result with a correspondingly large measuring error. Let us consider as an example an arrangement in which a temperature sensor is arranged on the side of the first resonator remote from a heat source. An increase in temperature has an effect on the measuring signal as soon as the side of the first resonator facing this heat source heats up; but this cannot be detected and compensated for until the side of the first resonator remote from the heat source heats up. In the intervening period, no satisfactory temperature compensation takes place.

The invention brings particular advantages when it is combined with a first resonator that is at least partly filled with a dielectric. The term "dielectric" here means a material having a dielectric constant of at least 2, preferably at least 5. Thus, for example, the temperature dependency of the measured variables of the first resonator is then determined decisively by the temperature dependency of the dielectric constant of the dielectric filling. Because of the frequently poor thermal conductivity properties of dielectric materials, a spatially non-homogeneous temperature distribution or a time-variant heat load has a particularly strong effect, since it can take a long time for a stationary temperature distribution to form. The second resonator is accordingly preferably likewise at least partly filled with a corresponding dielectric that has a temperature distribution comparable with that of the dielectric filling of the first resonator at every instant of the measurement.

The second resonator preferably has properties in relation to the response to the environmental influences and disturbance variables comparable with those of the first resonator. Thus, the first resonator and the second resonator are advantageously of substantially the same construction. That may apply, for example, to the dimension and the material or materials of the resonators, for example, in respect of the thermal conductivity, the thermal penetration value, heat transfer, heat transmission, thermal capacity, thermal expansion and/or other thermally relevant variables. When the properties of the first resonator to be compensated are dominated by one material, for example, a dielectric filling, it is generally sufficient for the appropriate properties in relation to this material to correspond.

The first and the second resonator are preferably arranged adjacent to one another and/or form a modular unit; in that way it is possible to ensure that both resonators are exposed to substantially the same environmental influences and disturbance variables. Alternatively, however, the two resonators can be arranged spatially separate from one another.

A further great advantage of the invention is the fact that the second resonator can advantageously also be used for simultaneous compensation of the influence of further disturbance variables, for example, drifting of the electronics in the longer term or material changes as a consequence of ageing.

The product temperature has a direct influence on the measuring signal owing to the temperature dependency of the dielectric constant of the product. The arrangement can therefore advantageously contain an additional temperature sensor, for example, a PT-100 element or a thermometer measuring without contact, for direct and rapid measurement of the product temperature, in order to be able to correct the measuring signal correspondingly in a manner known per se.

The invention is applicable basically both in the case of a first resonator operating on the basis of transmission measurement and in the case of a first resonator operating on the basis of reflection measurement.

Advantageously, the first resonator and the second resonator are at least partly filled with a dielectric ($\in_r > 2$). Advantageously, the first resonator and the second resonator are fed with microwaves of the same frequency.

Advantageously, the product runs through the first resonator. Advantageously, the first resonator and/or the second resonator are substantially completely shielded cavity resonators with openings for the admission of samples.

The invention furthermore includes an advantageous apparatus for the use according to the invention and/or for implementing the measuring method according to the invention, especially for measuring the density of at least one sliver of textile fibres, for example, of cotton, synthetic fibres or the like, in which the microwave measuring arrangement is used for control and/or regulation of a processing device for at least one textile fibre sliver.

The microwave measuring device is advantageously arranged at the delivery end of a card. At least one microwave measuring arrangement is preferably arranged at the feed end and/or at the delivery end of the drawing system of a draw frame. The drawing system is advantageously a card drawing system at the delivery end of a card. The textile fibre sliver is preferably a card sliver. The textile fibre sliver is advantageously a draw frame sliver. The microwave measuring arrangement is preferably connected to an electronic control and regulating device, for example, a machine control and regulating device. The control and regulating device is advantageously connected to at least one actuator, for example, drive motor, for changing the density of the fibre sliver. An indicating device, for example, display screen, printer or the like, for displaying the density of or density changes in the fibre sliver is preferably connected to the control and regulating device. The microwave measuring arrangement is advantageously used to monitor the density of a sliver produced on a card or draw frame.

A further application case is the measurement of the head compression (area of relatively high density of the tobacco in a cigarette) during the process of manufacturing a cigarette in a cigarette machine.

The invention also provides a method of controlling the density of fibre material in a textile processing machine, comprising monitoring the fibre material at a measuring location using a device comprising a first resonator and a compensation device for compensating environmental influences on said first resonator, said compensation device comprising a second resonator, and adjusting the condition of a processing step ins aid machine in dependence on measured values obtained by the measuring device.

DESCRIPTION OF THE PREFERRED EMBODIMENTS

Figure 1:
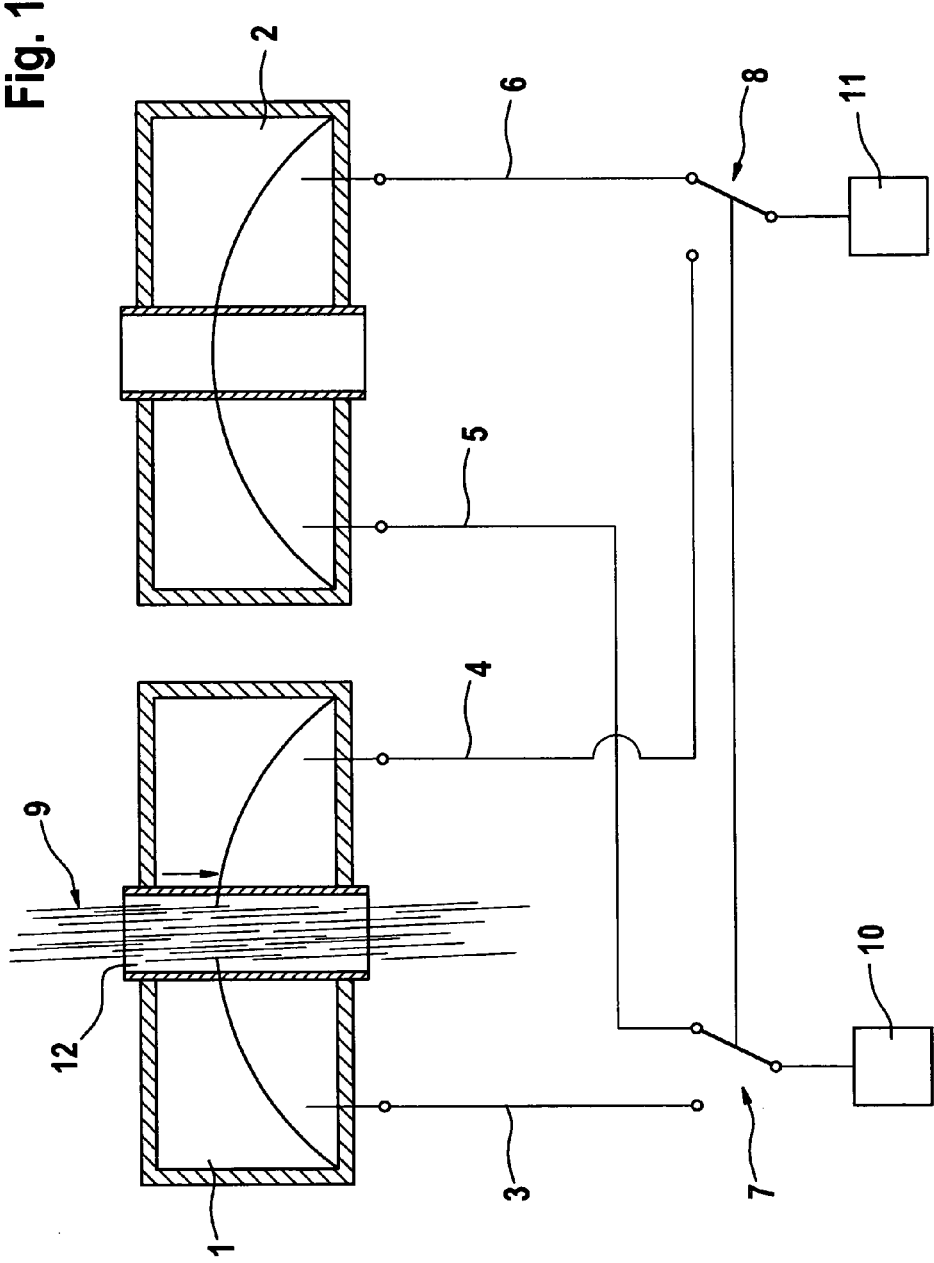
FIG. 1 is a cross-sectional view of a construction of a measuring arrangement according to the invention with spatially separated resonators.
Figure 2:
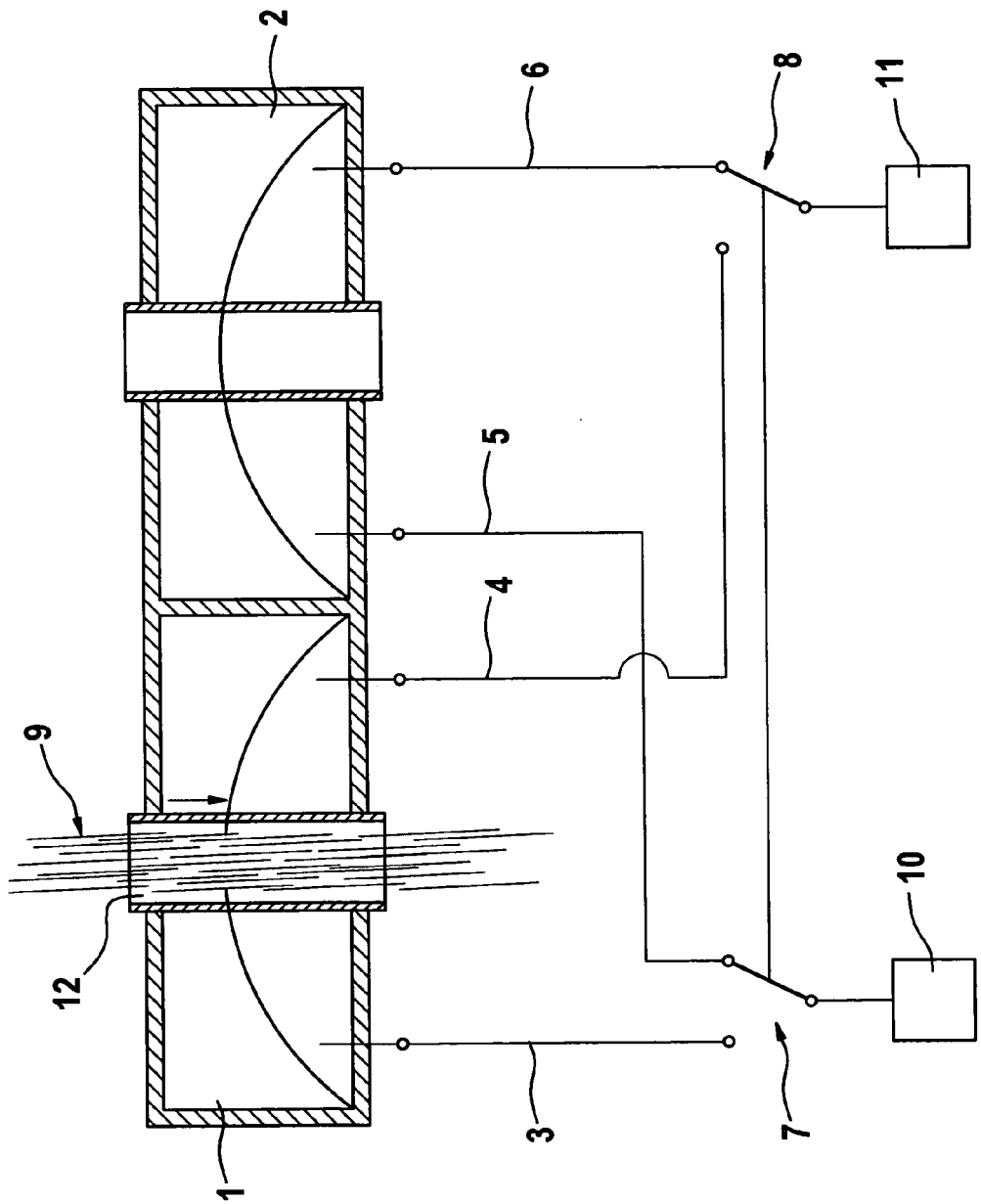
FIG. 2 is a cross-sectional view of a construction of a measuring arrangement according to the invention in which the two resonators are adjacent to each other and form a modular unit.

Referring first to FIGS. 1 and 2, FIG. 1 shows a spaced measuring arrangement and FIG. 2 shows a modular measuring arrangement, each of which consists of a microwave sensor 1 (measuring resonator) and a compensating device 2 (reference resonator). Except for the fact that the sensor 1 and device are spaced in FIG. 1 and modular in FIG. 2, the construction of those two embodiments is essentially the same and the following description is to be understood as referring to both FIGS. 1 and 2.

The product is guided through two openings through the microwave sensor 1.

Microwaves are generated by means of suitable devices 10 (microwave generators), and fed into the resonator 1 via a connection 3. At a specific frequency, standing waves are induced in the resonator 1. The distribution of the field strength in the region of the resonator 1 is indicated schematically in FIGS. 1 and 2. Microwaves enter the product area 12 and can interact with a product 9 located therein. The microwaves are output via a connection 4 and passed to a downstream evaluating device 11 (microwave generator). The reference resonator 2 is arranged directly adjacent to the measuring resonator 1.

Microwaves that are preferably tapped off from the infeed 10 by means of the switch 7 are injected into and fed out of the reference resonator 2 via connections 5 and 6. The microwaves are passed to the evaluating unit 11 via the switch 8. The switching frequency of the switches 7 and 8 can be as high as desired. Because the reference resonator and the measuring resonator are of the same construction, the conditions obtaining in the two resonators 1, 2 are substantially the same at all times, e.g. the temperature distribution is approximately the same.

For measurement, the frequency of the field in the resonator 1 is driven through a range that contains a specific, isolated resonance. The range to be passed through depends inter alia on the product in question and on the humidity and temperature values occurring in practice (owing to the magnitude of the resonance shift consequent thereon). From the starting signal, the resonant frequency $f_1$ and the half-value width $\Gamma_1$ of the measured resonance are determined in an evaluating unit. Such a measuring and evaluating cycle can take place in a fraction of a second.

At specific times, a corresponding measurement is effected in the reference resonator 2. The frequency of the field in the reference resonator 2 is driven through a range that contains a specific, isolated resonance; the resonant frequency $f_2$ and the half-value width $\Gamma_2$ are likewise determined. The values $f_2$, $\Gamma_2$ are independent of the product density by virtue of the arrangement of the reference resonator 2. The values $f_2$, $\Gamma_2$ are subsequently converted into corresponding values $f_0$, $\Gamma_0$ on the basis of two calibration curves stored in the evaluating unit. The values $f_0$, $\Gamma_0$ denote the resonant frequency and the half-value width respectively of the resonator 1 without product (measurement with no load). These calibration curves, which clearly define the correlation between the variables $f_2$ and $f_0$ and between the variables $\Gamma_2$ and $\Gamma_0$ for a specific product material, are initially determined in corresponding calibration measurements by variation in the environmental influences and specific disturbance variables within a range occurring in practice. In operation, no-load measurements to determine the variables $f_0$, $\Gamma_0$ can then be omitted, which is of advantage particularly in the case when measurements are being carried out on a product stream, where no-load measurements are possible only when the product stream is interrupted.

From the variables mentioned, there is formed in a manner known per se a variable $\Psi(A)=f((f_1-f_0); (\Gamma_1-\Gamma_0)$ dependent only on the material density A, and independent of the moisture content of the material; and further—owing to the invention—being independent of environmental influences and specific disturbance variables. The material density A is determined from the variable $\Psi$ by means of a calibration curve stored in the evaluating unit. This calibration curve, which clearly defines the correlation between the variables A and $\Psi$ for a specific product material, is first of all determined in a corresponding calibration measurement by variation of the product density within a range occurring in practice.

The measurements in the measuring resonator 1 and in the reference resonator 2 are carried out preferably at approximately comparable frequencies in order to avoid dispersion influences. The reference resonator 2 is accordingly preferably dimensioned so that the frequency ranges to be passed through in the case of the measuring resonator 1 and the reference resonator 2 have a mean spacing of less than 1 GHz, preferably less than 100 MHz, additionally preferably less than 10 MHz. The measurements take place preferably in the frequency range from 0.1 to 20 GHz, additionally preferably 1 to 5 GHz, additionally preferably 2 to 3 GHz, additionally preferably 2.4 to 2.5 GHz.

Figure 3:
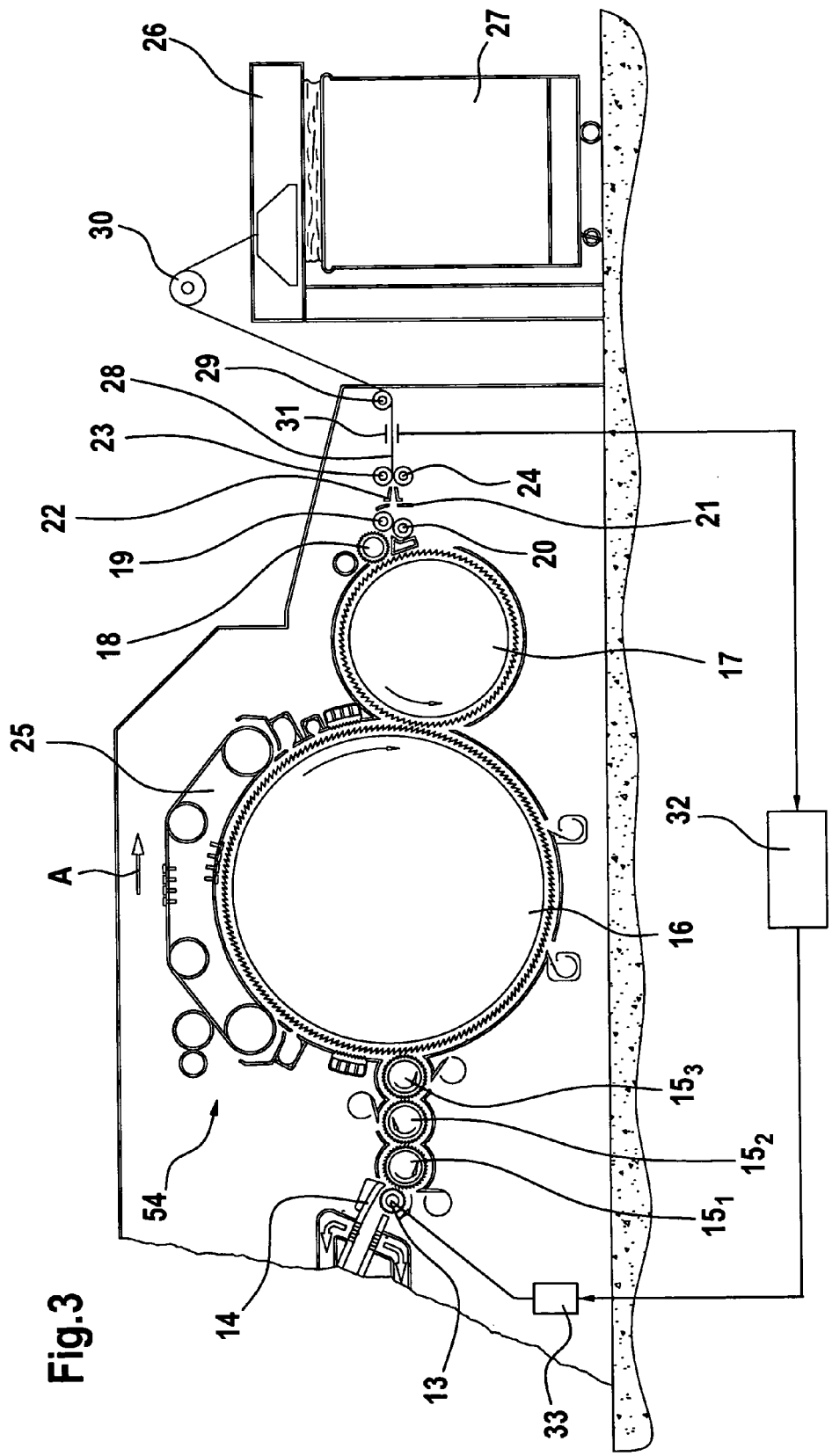
FIG. 3 is a diagrammatic side view of a card with a microwave measuring arrangement according to the invention.

FIG. 3 shows a carding machine 54, for example, a high-performance card DK 903 made by Trützschler GmbH & Co. KG of Mönchengladbach, Germany, with feed roller 13, feed table 14, licker-ins 15₁, 15₂, 15₃, cylinder 16, doffer 17, stripping roller 18, squeezing rollers 19, 20, web-guide element 21, web funnel 22, take-off rollers 23, 24, revolving card top 25, can coiler 26 and can 27. The directions of rotation of the rollers are shown by respective curved arrows. The take-off rollers 23, 24 draw off a card sliver 28, which passes over guide rollers 29, 30 to the can coiler 26 and from there is laid in the can 27. A microwave measuring arrangement 31 according to the invention (for example, one of those described above with reference to FIG. 1 or FIG. 2), is arranged between the take-off rollers 23, 24 and the guide roller 29. The microwave measuring arrangement 31 is connected to an electronic control and regulating device 32, for example, a microcomputer, which alters the rotational speed of the feed roller 13 by way of a variable speed drive motor 33. In this way, the density of the card sliver 28, which can leave the take-off rollers 23, 24 at high speed, for example, 200 m/min or more, is adjusted. The letter A denotes the direction of working.

Figure 4:
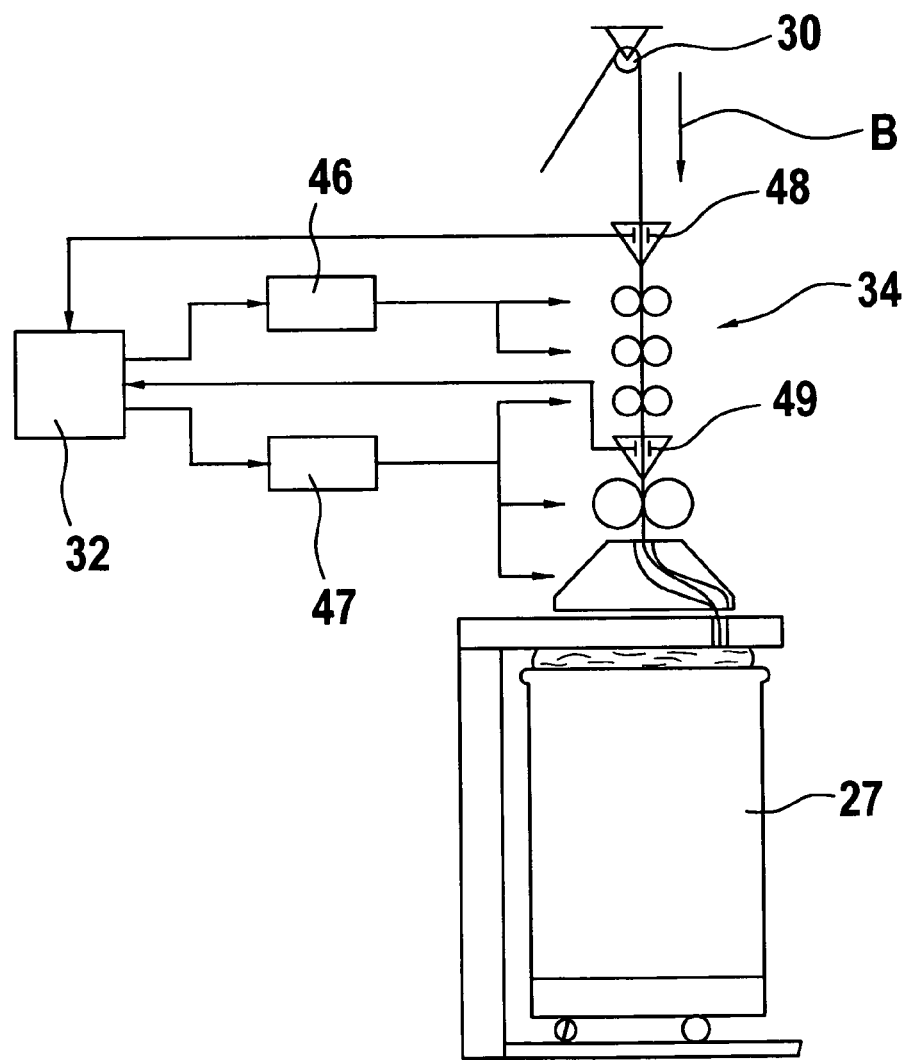
FIG. 4 is a diagrammatic side view of a can coiler with fibre sliver can with an autoleveller drawing system with a microwave measuring arrangement according to the invention.
Figure 5:
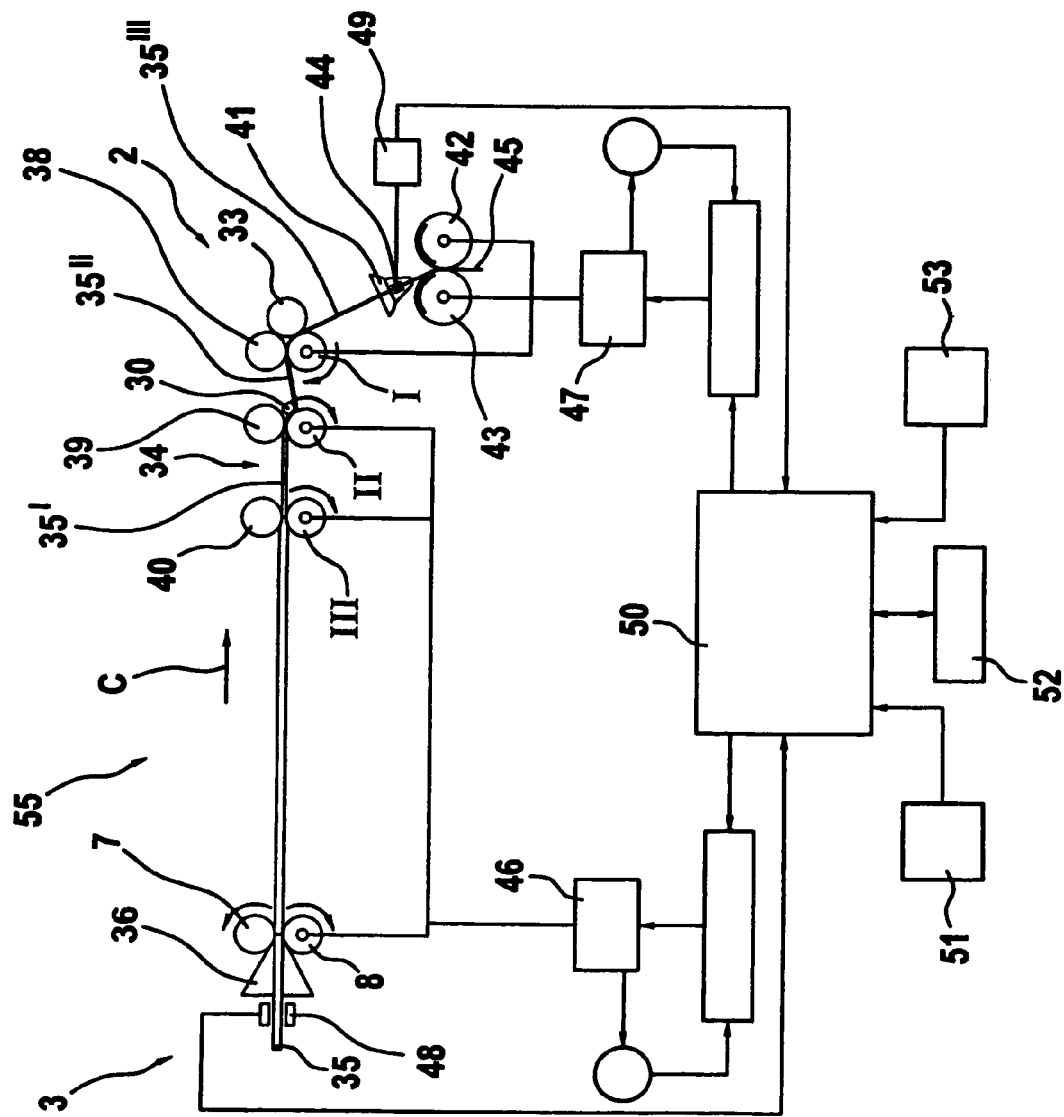
FIG. 5 is a diagrammatic side view of an autoleveller draw frame having a respective microwave measuring arrangement according to the invention as input and output measuring element.

In the embodiment of FIG. 4, a drawing system 34, which corresponds to the drawing system shown in FIG. 5, is arranged above the can coiler 26; reference is made to the description, further below, of the drawing system of FIG. 5. At the feed end and delivery end of the drawing system 34 there is a respective microwave measuring arrangement 48, 49, which are connected to the electronic control and regulating device 32, which is furthermore connected to drive motors 46, 47 for the drawing system 34 and to a drive motor 21 for the can turntable.

Referring to FIG. 5, a draw frame 55, for example, a draw frame HSR made by Trützschler GmbH & Co. KG, has a drawing system 34, upstream of which is a drawing system feed 34a and downstream of which is a drawing system outlet 34b. The fibre slivers 35 enter the sliver guide 36 from cans (not shown) and, drawn by the take-off rollers, are transported to the drawing system 34. The drawing system 34 is designed as a 4-over-3 drawing system, that is, it consists of three bottom rollers I, II, III (I being the bottom delivery roller, II being the bottom middle roller and III being the bottom feed roller) and four top rollers 33, 38, 39, 40. Drafting of the composite fibre sliver 35″, comprising several fibre slivers 35, takes place in the drawing system 34. The draft is made up from the preliminary draft and the main draft. The roller pairs 40/III and 39/II form the preliminary drafting zone and the roller pairs 39/II and 38, 33/I form the main drafting zone. The drawn fibre slivers 35‴ reach a web guide 41 at the outlet of the drawing system and are drawn by means of the take-off rollers 42, 43 through a sliver funnel 44 in which they are condensed to a fibre sliver 45, which is subsequently deposited in a can (not shown). The letter C denotes the working direction, and 35" denotes the fibre slivers in the drawing system. The take-off rollers, the bottom feed roller III and the middle bottom roller II, which are mechanically linked, for example, by way of toothed belts, are driven by the variable speed motor 46, it being possible to pre-set a desired value. (The associated top rollers 39 and 40 co-rotate). The bottom output roller I and the take-off rollers 42, 43 are driven by the main motor 47. At the inlet 34a to the drawing system, a variable proportional to the density of the fed-in fibre slivers 35 is measured by a feed-side measuring device 48 according to the invention. At the outlet 34b of the drawing system 34, the density of the fibre sliver is obtained by a delivery-side measuring device 49 according to the invention associated with the sliver funnel 44. A central computer unit 50 (control and regulating device), e.g. a microcomputer with microprocessor, determines a setting of the regulated variable for the variable speed motor 46. The measured variables of the two measuring devices 48 and 49 are sent during the drawing process to the central computer unit 50. From the measured variables of the feed-side measuring device 48 and from the desired value for the density of the emerging fibre sliver 45, the adjustment value for the variable speed motor 46 is determined in the central computer unit 50. The measured variables of the delivery-side measuring device 49 are used to monitor the emerging fibre sliver 45 (monitoring of delivered sliver). By means of this control system, fluctuations in the density of the fed-in fibre slivers 35 can be compensated by corresponding adjustments to the drafting process and the fibre slivers can be evened out. The reference numeral 51 denotes a display screen, 52 denotes an interface and 53 denotes an input means.

Figure 6:
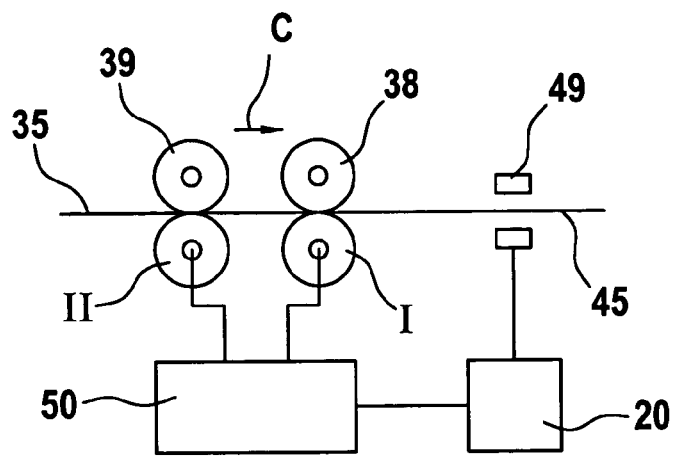
FIG. 6 shows an autoleveller draw frame with a closed control loop (regulation) and a measuring arrangement according to the invention.
Figure 7:
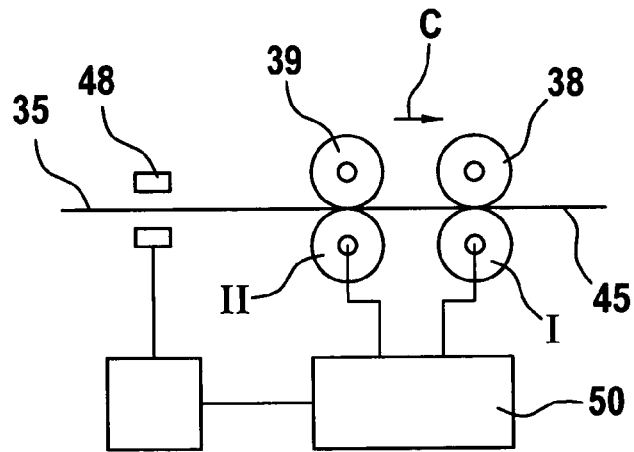
FIG. 7 shows an autoleveller draw frame with an open control loop (control)
Figure 8:
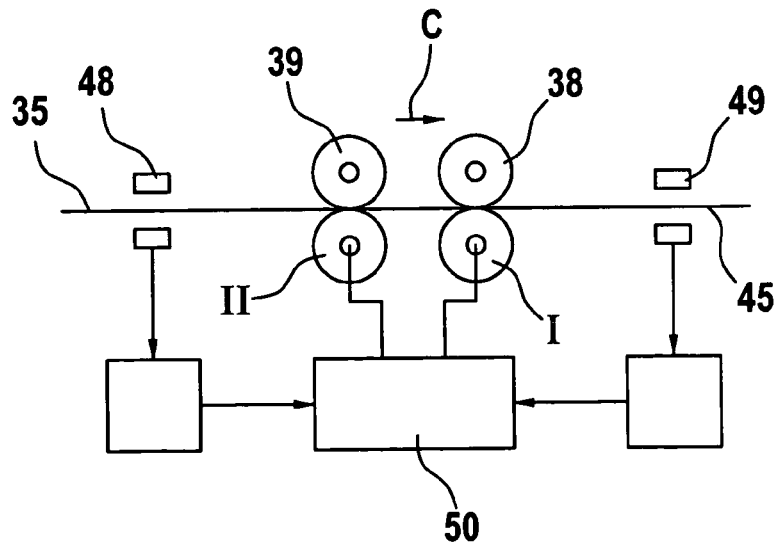
FIG. 8 shows an autoleveller draw frame with a combination of an open and a closed control loop (reference variable input) and two measuring arrangements according to the invention.

FIGS. 6, 7 and 8 show basic layouts of the drawing system of a draw frame with different constructions for the adjustment of the fibre sliver density. FIG. 6 shows a closed control loop, in which the microwave measuring arrangement 49 is arranged at the delivery end of the drawing system. The fibre material leaving the drawing system passes through the measuring arrangement 49, the output signal of which is compared in the control electronics 50 with a desired value and is converted so that a corresponding control signal is supplied to an actuator (variable speed motor 46, see FIG. 5) for the roller II. The output signal corresponding to the density of the emerging fibre material thus influences the speed ratio of the drafting roller pairs 39/II and 38/I in the sense that the fibre material is evened out. FIG. 7 shows an open control loop (open-loop control). Here, the microwave measuring arrangement 48 is located in the region in which the fibre material 35 approaches the drawing system, measures the density of the fibre material and the corresponding measuring signal is converted in the control electronics 50 into a control signal which is supplied to an actuator (variable speed motor 46, see FIG. 5) for the roller II. Allowances are made electronically for the time taken by the fibre material 35 to run from the measuring arrangement 48 to the drawing system. FIG. 8 shows a combination of an open and a closed control loop, in which the measuring signals of the measuring arrangement 49 are superimposed on the measuring signals of the measuring arrangement 48.

On a production machine, for example, a card 54 (FIG. 3) and draw frame 55 (FIG. 5) for the control and/or adjustment and also for monitoring the uniformity of the fibre slivers 28 and 45 produced, compensation of environmental influences and disturbance variables can be effected by the reference resonator 2, preferably during regular pauses in production and/or during machine stoppages, for example, can changes, in which measurements with the measuring resonator 1 are not required. The reference measurement in the reference resonator 2 can be effected at regular or irregular intervals. It may be sufficient for a measurement to be carried out in reference resonator 2 after several minutes, preferably at the latest after a few hours, if environmental influences or disturbance variables have only a correspondingly slow effect. The efficiency of the machine is not affected thereby.

When the change-over of the switches 7 and 8 (FIGS. 1 and 2) and the stabilisation of the electrical field in the resonators 1 and 2 is effected within a short time, correction of the microwave measuring arrangement can be effected within a correspondingly short time. In this way, environmental influences and disturbance variables can be compensated during ongoing production in a processing machine Although the foregoing invention has been described in detail by way of illustration and example for purposes of understanding, it will be obvious that changes and modifications may be practised within the scope of the appended claims.

What is claimed is:

1. A measuring device for monitoring a fibrous material and determining a parameter that is related to the dielectric properties of the fibrous material, comprising a product area for receiving a traveling strand of the fibrous material, wherein the product area is a channel, a first microwave resonator from which, in operation, microwaves can enter the product area, a compensation device for compensating for environmental influences during the monitoring of the fibrous material, the compensation device comprising a second microwave resonator which is shielded from the product area in respect of microwave radiation, and an evaluating unit alternatingly coupled to the first and second microwave resonators and adapted to receive and evaluate microwaves output from the first and second microwave resonators to determine the parameter related to the dielectric properties of the fibrous material, compensated for environmental influences.

2. A measuring device according to claim 1, in which the compensation device is arranged to compensate for temperature variation.

3. A measuring device according to claim 1, which is arranged to determine the density of the traveling strand of fibrous material.

4. A measuring device according to claim 1, in which the first resonator and the second resonator are of substantially the same construction.

5. A measuring device according to claim 1, in which the first resonator and the second resonator are at least partly filled with a dielectric.

6. A measuring device according to claim 1, in which the first resonator and the second resonator are arranged adjacent to each other, and separated by a space.

7. A measuring device according to claim 1, in which the first resonator and the second resonator form a modular unit.

8. A measuring device according to claim 1, in which, in operation, the traveling strand of fibrous material runs through the first resonator.

9. A measuring device according to claim 1, in which the first resonator and/or the second resonator are each a substantially shielded cavity resonator with an opening for the admission of the traveling strand of fibrous material.

10. A fibrous material processing machine having
at least one fibre processing elements and
a measuring device having
   a first microwave resonator from which, in operation, microwaves can enter a product area, and
   a compensating device comprising a second microwave resonator shielded from the product area in respect of microwave radiation, wherein the measuring device is positioned at a measuring location and the processing element of the machine is adjustable in dependence of measurement values obtained at the measuring location.

11. A machine according to claim 10, which is for processing textile fibre material, and in which the measuring device is arranged to monitor the density of a textile fibre sliver and the processing element is adjustable for influencing properties of the sliver.

12. A machine according to claim 10, the machine being a carding machine, and the measuring device being arranged near a delivery outlet of the carding machine.

13. A machine according to claim 10, which is a draw frame, the measuring device being arranged near a delivery outlet of the draw frame.

14. A machine according to claim 10, which is a draw frame, the draw frame comprising the measuring device in an inlet region and the compensating device in an outlet region.

15. A machine according to claim 14, comprising a machine control and regulation device to which the measuring device and the compensating device are connected.

16. A machine according to claim 15, further comprising an actuation device for the processing element, the actuation device being controllable by the control and regulation device in dependence on measurement data received from the measuring device and/or measurement data received from the compensating device.

17. A method of controlling the density of fibre material in a textile processing machine, comprising
   monitoring the fibre material at a measuring location using a measuring device comprising a first resonator and a compensation device, the compensation device comprising a second resonator shielded from the fibre material in respect of microwave radiation, and
   adjusting the machine in dependence on measured values obtained by the measuring device.

* * * * *